United States Patent [19]

Riederer

[11] Patent Number: 4,599,437

[45] Date of Patent: Jul. 8, 1986

[54] CONTINUOUS PROCESS FOR VARYING MOLECULAR WEIGHT OF ORGANOPOLYSILOXANES

[75] Inventor: Manfred Riederer, Burghausen, Fed. Rep. of Germany

[73] Assignee: Wacker-Chemie GmbH, Fed. Rep. of Germany

[21] Appl. No.: 767,157

[22] Filed: Aug. 19, 1985

[30] Foreign Application Priority Data

Oct. 29, 1984 [DE] Fed. Rep. of Germany ....... 3439543

[51] Int. Cl.$^4$ ................................................ C07F 7/08
[52] U.S. Cl. .................................... 556/462; 556/456; 528/16; 528/12; 528/23
[58] Field of Search ............................... 556/462, 456

[56] References Cited

U.S. PATENT DOCUMENTS 2,467,976  4/1949  Hyde ............................... 556/462 X
3,274,154  9/1966  Kendrick et al. ................ 556/462 X
3,853,934  12/1974 Sicilliano et al. .................... 556/462
3,937,684  2/1976  Razzano ........................... 556/462 X
4,426,508  1/1984  Dromard et al. ................ 556/462 X Primary Examiner—Paul F. Shaver
Attorney, Agent, or Firm—Bierman, Peroff & Muserlian

[57] ABSTRACT

In a process for varying the molecular weight of linear or cyclic organopolysiloxanes in the presence of a catalyst which is solid in the reaction mixture at the reaction temperature, the improvement comprising that the catalyst which is solid in the reaction mixture at least at the respective reaction temperature and the organopolysiloxane whose molecular weight is to be changed are continuously and simultaneously passed through a heated cylindrical reactor whose contents is mechanically moved, the reactor having a length to inside diameter ratio of 1:1 to 20:1 and its interior pressure being held at 50 to 500 hPa (abs.) and the catalyst is removed from the mixture after leaving the reactor.

5 Claims, No Drawings

CONTINUOUS PROCESS FOR VARYING MOLECULAR WEIGHT OF ORGANOPOLYSILOXANES

STATE OF THE ART

British patent Nos. 1,488,369 and 1,488,370 describe a continuous process for varying the molecular weight of linear and cyclic organopolysiloxanes with a catalyst which is solid in the reaction mixture at least at the reaction temperature and which is carried out at reduced pressures, atmospheric pressure and super atmospheric pressures and both processes use a solid bed catalyst.

OBJECTS OF THE INVENTION

It is an object of the invention to provide a novel continuous process for varying the molecular weight of linear and cyclic polysiloxanes with a catalyst solid in the reaction mixture at least at the reaction temperature using an especially simple apparatus with especially high space-time yields or especially short residence times.

It is another object of the invention to provide a novel process for reacting linear or cyclic organopolysiloxanes with sufficient effective catalyst in the presence of an organosilicon compound capable of regulating the chain length to obtain linear organopolysiloxanes containing less than 30 weight-ppm of silicon bound hydroxyl groups.

These and other objects and advantages of the invention will become obvious from the following detailed description.

THE INVENTION

The novel process of the invention for varying the molecular weight of linear or cyclic organopolysiloxanes in the presence of a catalyst which is solid in the reaction mixture at the reaction temperature, the improvement comprises that the catalyst which is solid in the reaction mixture at least at the respective reaction temperature and the organopolysiloxane whose molecular weight is to be changed are continuously and simultaneously passed through a heated cylindrical reactor whose contents is mechanically moved, the reactor having a length to inside diameter ratio of 1:1 to 20:1 and its interior pressure being held at 50 to 500 hPa (abs.) and the catalyst is removed from the mixture after leaving the reactor.

The catalysts solid in the reaction mixture at least at the respective reaction temperature which may be used in the process of the invention are any desired catalysts solid in the reaction mixture at least at the respective reaction temperature which have been used in the known processes for varying the molecular weight of linear or cyclic organopolysiloxanes by catalyst solid in the reaction mixture at least at the respective reaction temperature.

Especially preferred as solid catalyst for the process of the invention, because it allows especially short residence times, are commercially available acid-activated montmorillonites. Generally, acid-activated bleaching earths are preferred as catalysts in the process of the invention. Examples of commercially available acid-activated bleaching earths other than acid-activated montmorillonites are "Terrana L 80", "Tonsil AC", "Clarit Standard A", "Nordal", "Filtrol Ultra" and "Rumsil".

Other examples for catalysts solid in the reaction mixture at least at the respective reaction temperatures are kaolin, active carbon, aluminum silicates with molecular sieve structure, sulfonated carbon, acid-activated carbon black, sulfonated styrenedivinylbenzene copolymers, aluminum powders and cation-exchanging polymers with sulfonyl containing side chains, the sulfonyl groups being bound to a carbon atom carrying at least one fluorine atom. One type of catalyst solid in the reaction mixture at least at the respective reaction temperature may be used but mixtures of at least two different kinds of such catalysts may also be used, e.g., mixtures of acid-activated montmorillonite and acid-activated carbon black.

The particle size of the catalysts solid in the reaction mixture at least at the respective reaction temperature as used in the process of the invention is preferably at most 180 micrometers. Preferably, solid catalyst is used in the process in amounts of 0.1 to 30 percent by weight, based on the total weight of the organosilicon compounds introduced into the heated cylindrical reactor simultaneously with this catalyst.

Examples of linear or cyclic organopolysiloxanes whose molecular weight is to be changed as starting materials in the process of the invention are any desired linear or cyclic organopolysiloxanes which it has been possible to use in the known continuous processes for varying the molecular weight of linear or cyclic organopolysiloxanes with catalyst solid in the reaction mixture of the respective reaction temperature. Examples of preferred organopolysiloxanes are those of the formula

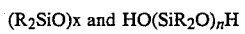

$(R_2SiO)x$ and $HO(SiR_2O)_nH$ wherein R is a monovalent, optionally substituted hydrocarbon, or hydrogen with the provision that at most one hydrogen atom is bound to one silicon atom, x is an integer of 3 to 8, and n is integer of 1, preferably at least 2, to at most that value which corresponds to an average viscosity of at most 1000 mPa/s at 25° C.

Examples of hydrocarbon for R are methyl, ethyl, vinyl and phenyl. Examples of substituted hydrocarbons for R are preferably halogenated hydrocarbons such as 3,3,3-trifluoropropyl and chlorophenyl, as well as aliphatics comprised of carbon, hydrogen, ether oxygen, and fluorine such as 1,1,2,2,3,3,3-hexafluoropropyloxypropyl and 1,1,2,2-tetrafluoroethyloxypropyl. Because of easier accessibility, preferably at least 80% of the hydrocarbons R are methyls.

There may be used in the process of the invention one type of organopolysiloxane whose molecular weight is to be changed as well as mixtures of at least two different types of such organopolysiloxanes may be used, so that simultaneously with the change of the molecular weight an equilibration of different organopolysiloxanes can take place.

In the process of the invention, organosilicon compounds which regulate the chain length may be used additionally in which any desired chain length-regulating organosilicon compounds may be used which have been used additionally in the known methods for the variation of the molecular weight of linear or cyclic organopolysiloxanes. Preferred examples of such chain length-regulating organosilicon compounds are those of the formula

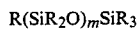

$$R(SiR_2O)_mSiR_3$$

wherein R has the above definition and m is an integer of 1 to 50, as well as those of the formula

$$(R_3Si)_2NH$$

wherein R again has the above definition. Important specific examples of such compounds are hexamethyldisiloxane, 1,3-divinyl-1,1,3,3-tetramethyldisiloxane, 1,3-dihydrogen-1,1,3,3-tetramethyldisiloxane and hexamethyldisilazane.

The amount of organosilicon compounds regulating the chain length depends, as is well known in the art, on the desired chain length. The greater the amount of additionally used, chain length regulating organosilicon compound is, the lower will be the viscosity of the obtained organopolysiloxanes. This quantity is preferably at least sufficiently large that the organopolysiloxanes obtained in the process of the invention have an average viscosity of at most 50,000 mPa/s at 25° C. and hence can easily be removed from the catalyst by filtering.

The catalyst can be introduced into the reactor in the process of the invention separate from silicon compound employed in the process. Alternatively, a pumpable mixture of catalyst solid in the reaction mixture at least at the respective reaction temperature and the organosilicon compound may be introduced into the reactor. Such a pumpable mixture can be prepared, for example, in that catalyst and organosilicon compound(s) are mixed by means of a stirrer in at least one reactor, possibly raising the temperature to preferably up to 60° C.

If the organopolysiloxane whose molecular weight is to be increased was not already heated during mixing with the catalyst, the organopolysiloxane or a mixture of catalyst and organopolysiloxane not already heated during mixing whose molecular weight is to be changed can be heated to preferably up to 105° C. before introduction into the heated cylindrical reactor, e.g. in a heat exchanger.

The heated cylindrical reactor is preferably a tube which is heated by a jacket around this tube. Preferably, the ratio of length to inside diameter is 6:1 to 8:1, preferably 7:1 or approximately 7:1. Preferably, the reactor used in the process of the invention is heated to such an extent that the temperature of its contents is 80° to 180° C., preferably 120° to 140° C.

The mechanical motion of the contents of the heated cylindrical reactor preferably is effected with an agitator having at least two vanes or another stirring means suitable for the movement of the reactor content with which the reactor is equipped. Preferably, the stirring speed is 800 to 1200 revolutions per minute. The reactor may be arranged vertically or horizontally, preferably vertically. If it is arranged vertically, a pumpable mixture of catalyst and organosilicon compound(s) is, in a preferred form of the process of the invention, introduced into the reactor from below by a proportioning pump and at the upper end of the reactor, the mixture of organopolysiloxane and catalyst is removed from the reactor by a vacuum-proof pump, e.g. a gear pump, there being present above the outlet for the mixture of organopolysiloxane and catalyst issuing from the reactor a descending condenser in which the water formed during the condensation of silicon bound hydroxyl groups in the reactor condense and which is connected to the pump which maintains the interior of the reactor at a pressure of 50 to 500 hPa (abs.). If the pressure inside the reactor is less than 50 hPa (abs.), too much cyclic organopolysiloxane is discharged together with the water and too many cyclic organopolysiloxanes continue to form in the reactor for the establishment of the equilibrium. If the pressure in the interior of the reactor is more than 500 hPa (abs.), the space-time yields are not high enough.

If the catalyst is not introduced into the reactor in admixture with the organopolysiloxane whose molecular weight is to be changed, although the use of such a mixture is preferred because of the greater simplicity, it can be introduced into it e.g. at the upper end of the reactor by means of a proportioning screw. Residence times of the mixture of catalyst and organosilicon compound(s) in the reactor of at most 5 minutes are usually sufficient.

The removal of the catalyst mixture leaving the reactor can be effected in any desired manner suitable for separating solids from suspensions and widely known, e.g. filtering or centerfuging, this being preferably carried out continuously also. The catalyst thus separated can be used again in the process of the invention, possibly after mixing with fresh catalyst. After the catalyst with the above stated parameters had been used in the process of the invention ten times and recycled in the process after the separation from the organopolysiloxane, no reduction of its effectiveness was observed.

If not too readily volatile organosilicon compounds are used, the introduction of gases such as air or nitrogen, which are inert to the liquid and solid substances used in the process, occurring simultaneously through the reactor, may have the advantage that the catalyst remains active still longer.

The organosilicon compounds with a lower boiling point than the desired organopolysiloxane final product may be removed by distillation of the organopolysiloxane after removal of the solid catalyst and can be recycled to the reactor for reuse in the process.

In the following examples there are described several preferred embodiments to illustrate the invention. However, it is to be understood that the invention is not intended to be limited to the specific embodiments. The acid-activated montmorillonite used in the examples had a bulk density of 450±40 g/l, a weight after shaking of 670±60 g/l, a specific gravity of about 2.4 kg/l, a moisture content (2 hours at 110° C.) of a maximum of 10% by weight, a loss on ignition (1000° C.) of a maximum of 7% by Weight and a pH of 2.5 to 3 in a 10% aqueous suspension. It is comprised of silicon dioxide, aluminum oxide, ferric oxide, magnesium oxide, sodium oxide and potassium oxide and 80% by weight passes through a screen with a clear mesh width of 60 μm.

EXAMPLE 1

A stirred mixture of 3 parts by weight of acid-activated montmorillonite, 5.4 parts by weight of hexamethyldisiloxane and 100 parts by weight of dimethylpolysiloxane having a silicon bound hydroxyl in each terminal unit and a viscosity of 140 mPa at 25° C. at room temperature was continuously passed first through a heat exchange with an adjustable diaphragm pump at a rate of 6,720 ml per hour wherein it was heated to 105° C. and then was introduced into the bottom of a vertically arranged cylindrical reactor with a height of 385 mm, an inside diameter of 57 mm and a volume of 981 ml. The mixture had a residence time of 4.4 minutes since the liquid content of the reactor was continuously removed from the upper end of the reactor by means of a gear pump. The reactor contents were kept at 130° C. by a heating jacket about the reactor and the contents thereof were mechanically moved through the reactor with a laboratory stirrer at 1000 rpms. Above the reactor outlet for removal of organopolysiloxane and catalyst, there was provided a descending condenser in which substantially only water was condensed and a pump was connected thereto to maintain the pressure in the reactor interior at 180 hPa (abs.).

The product issuing from the reactor was vacuum filtered to remove the solid catalyst and the fractions of the filtrate boiling below 150° C. at 0.5 hPa (abs.) were distilled. The catalyst and the said low boiling fractions were recycled to the reactor to reduce the amount of dimethylpolysiloxane feed with terminal hydroxyl pumps by the amount of low boiling fraction recycled.

The distillation residue was approximately 90 parts by weight of dimethylpolysiloxane end blocked by trimethylsiloxy groups with a viscosity of 50 mPa/s at 25° C. The said organopolysiloxane contained less than 30 weight-ppm of silicon bound hydroxyl groups and after heating the same for 16 hours at 200° C., the viscosity variation of the product was only 2 mPa/s at 25° C.

EXAMPLE 2

The procedure of Example 1 was repeated except that only 1.9 parts by weight of hexamethyldisiloxane was used in place of the 5.4 parts by weight of Example 1 and about 90 parts by weight of dimethylpolysiloxane end blocked by trimethylsiloxy groups having a viscosity of 250 mPa/s at 25° C. were obtained. The said organopolysiloxane contained less than 30 by weight-ppm of silicon bound hydroxyl groups and after heating the product at 200° C. for 16 hours, the viscosity variation was only 2 mPa/s at 25° C.

EXAMPLE 3

The procedure of Example 1 was repeated except that only 1.0 parts by weight of hexamethyldisiloxane was used in place of the 5.4 parts by weight of Example 1 and about 90 parts by weight of dimethylpolysiloxane end blocked by trimethylsiloxy groups having viscosity of 1000 mPa/s at 25° C. were obtained. The said organopolysiloxane contained less than 30 by weight ppm of silicon bound hydroxyl groups and after heating the product at 200° C. for 16 hours, the viscosity variation of the product was only 20 mPa/s at 25° C. or only 2% of 1000 mPa/s.

COMPARISON EXAMPLE

The procedure of Example 3 was repeated except that the reactor pressure was not 180 mPa(abs.) but atmospheric pressure or about 1000 hPa(abs.) and only 1380 ml per hour of the mixture were added to the reactor resulting in a residence time of 21.7 minutes. Again, about 90 parts by weight of dimethylpolysiloxane end blocked by trimethylsiloxy groups were obtained but the said organopolysiloxane had a viscosity of only 280 mPa/s which indicates insufficient equilibration despite the much longer residence time (about 5 times longer).

EXAMPLE 4

The procedure of Example 1 was repeated except that the 11.1 parts by weight of hexamethyldisiloxane and 100 parts by weight of octamethylcyclotetrasiloxane were used in place of the 5.4 parts by weight of hexamethyldisiloxane and 100 parts by weight of linear dimethylpolysiloxane, respectively. About 90 parts by weight of dimethylpolysiloxane end blocked with trimethylsiloxy groups with a viscosity of 20 mPa/s at 25° C. were obtained.

EXAMPLE 5

The procedure of Example 1 was repeated except that 11.3 parts by weight of dimethylpolysiloxane end blocked by trimethylsiloxy groups with a viscosity of 20 mPa/s at 25° C. were used in place of the 5.4 parts by weight of hexamethyldisiloxane. About 90 parts by weight of dimethylpolysiloxane end blocked by trimethylsiloxy groups with a viscosity of 1000 mPa/s at 25° C. were obtained and the said organopolysiloxane contained less than 30 weight-ppm of silicon band hydroxyl groups.

Various modifications of the process of the invention may be made without departing from the spirit or scope thereof and it is to be understood that the invention is intended to be limited only as defined in the appended claims.

What I claim is:

1. In a process for varying the molecular weight of linear or cyclic organopolysiloxanes in the presence of a catalyst which is solid in the reaction mixture at the reaction temperature, the improvement comprising that the catalyst which is solid in the reaction mixture at least at the respective reaction temperature and the organopolysiloxane whose molecular weight is to be changed are continuously and simultaneously passed through a heated cylindrical reactor whose contents is mechanically moved, the reactor having a length to inside diameter ratio of 1:1 to 20:1 and its interior pressure being held at 50 to 500 hPa (abs.) and the catalyst is removed from the mixture after leaving the reactor.

2. The process of claim 1 wherein the catalyst solid in the reaction mixture at the reaction temperature is an acid-activated bleaching earth.

3. The process of claim 1 wherein the catalyst solid in the reaction mixture at the reaction temperature is acid-activated montmorillonite.

4. The process of claim 1 wherein the particle size of the catalyst is at most 180 mm.

5. The process of claim 1 wherein the amount of catalyst is 0.1 to 30% by weight based on the total weight of organosilicon compound.

* * * * *